United States Patent [19]

Kondo et al.

[11] Patent Number: 5,290,680

[45] Date of Patent: Mar. 1, 1994

[54] MONOCLONAL ANTIBODY, METHOD OF PRODUCTION THEREOF AND USE THEREOF

[75] Inventors: Koichi Kondo, Kizu; Takahisa Kobayashi; Makoto Katsuno, both of Matsumoto, all of Japan

[73] Assignee: Takeda Chemical Industries, Ltd., Osaka, Japan

[21] Appl. No.: 904,145

[22] Filed: Jun. 25, 1992

[30] Foreign Application Priority Data

Jun. 28, 1991 [JP] Japan .................... 3-158216

[51] Int. Cl.$^5$ .................... C12Q 1/00; G01N 33/535
[52] U.S. Cl. .................... 435/7.9; 435/70.21; 435/172.2; 435/240.27; 436/548; 530/388.24
[58] Field of Search ............ 435/7.9, 172.2, 70.21, 435/240.27; 530/388.24; 436/548

[56] References Cited

FOREIGN PATENT DOCUMENTS 3218269 11/1983 Fed. Rep. of Germany .

OTHER PUBLICATIONS

A. Edlund et al., "Cardiac Formation of Prostacyclin During Cardioplegia in Man", Prostaglandins, vol. 24, No. 1, Jul. 1982, pp. 5–19.
C. Machleidt et al., "Formation and Elimination of Proostacyclin Metabolites in the Cat in vivo as Determined by Radioimmunoassay of Unextracted Plasma", Chem. Abs., vol. 95, No. 21, Nov. 23, 1981.
Machleidt et al—European J. of Pharmacol, vol. 74 (1981) pp. 19–26.
Forder et al.—Chem. Abst., vol. 100 (1984), p. 29785d.
Gruetzmann et al.—Chem. Abst., vol. 100 (1984), p. 62512k.
Brune et al.—Chem. Abst., vol. 103 (1985), p. 65097b.

*Primary Examiner*—Sam Rosen
*Attorney, Agent, or Firm*—Wegner, Cantor, Mueller & Player

[57] ABSTRACT

The present invention relates to a monoclonal antibody which specifically recognizes 6,15-diketo-13,14-dihydro-prostaglandin $F_1\alpha$ with high sensitivity, a hybridoma producing said monoclonal antibody, a method of establishing said hybridoma and an immunoassay method for 6,15-diketo-13,14-dihydro-prostaglandin $F_1\alpha$ using said monoclonal antibody.

The monoclonal antibody of the present invention makes it possible to conveniently measure 6,15-diketo-13,14-dihydro-prostaglandin $F_1\alpha$, a stable metabolite of prostaglandin $I_2$ thought of as reflecting the concentration changes therein, with specificity and high sensitivity. It is useful in determining the content of prostaglandin $I_2$, which exhibits platelet aggregating inhibitory activity, vasodilating activity and other activities, in biological samples.

25 Claims, 2 Drawing Sheets

MONOCLONAL ANTIBODY, METHOD OF PRODUCTION THEREOF AND USE THEREOF

FIELD OF THE INVENTION

The present invention relates to a monoclonal antibody against 6,15-diketo-13,14-dihydro-prostaglandin $F_1\alpha$ (also referred to as 6,15-DK-13,14-DH-PGF$_1\alpha$ for short), a method of production thereof and a use thereof. The invention also provides a hybridoma producing said monoclonal antibody.

BACKGROUND OF THE INVENTION

Prostacyclin (prostaglandin $I_2$, also referred to as PGI$_2$ for short), a bioactive substance belonging to the arachidonic acid cascade, possesses potent platelet aggregation suppressive action, vasodilating action and other bioactivities. The bioactivities of PGI$_2$ are antagonistic to thromboxane $A_2$ (also referred to as TXA$_2$ for short); its measurement in vivo has been much emphasized. However, PGI$_2$ is an unstable substance, whose half-life at 37° C. is reportedly about 5 minutes. For this reason, 6-keto-prostaglandin $F_1\alpha$ (also referred to as 6-K-PGF$_1\alpha$ for short), which is derived from PGI$_2$ in the absence of enzyme, has been measured in place of PGI$_2$ (ALAN R. BRASH et al., J. Pharmacol. Exp. Ther., 226, 78 (1983)).

However, because of their low production rates and short half-lives, the concentrations of 6-K-PGF$_1\alpha$ in human plasma obtained under resting conditions are in the low picogram range (FitzGerald, G. A. et al., Circulation, 67, 1174–1177 (1983)). Moreover, sampling-induced artifacts and ex vivo synthesis by blood cells make most plasma measurements of primary icosanoids totally unreliable (Carlo Patrono et al., Advances in Prostaglandin, Thromboxane, and Leukotriene Research, Vol. 15, p. 71–73 (1985), edited by O. Hayaishi and S. Yamamoto, Raven Press, New York). Therefore, because the values of 6-K-PGF$_1\alpha$ obtained vary widely among institutions, comparison by absolute values has been almost impossible among different institutions [M. Suzuki et al., Japanese Journal of Clinical Medicine, Vol. 43, p. 1082 (1985)].

One method of circumventing such problems is measurement of metabolites that have an extended half-life. Although the 6,15-DK-13,14-DH-PGF$_1\alpha$ metabolite of PGI$_2$ has a longer half-life than 6-K-PGF$_1\alpha$, it was expected to precisely reflect changes in PGI$_2$ concentration [C. Patrono et al., Clinical Research, Vol. 29, p. 276A (1981)].

The object of the present invention is to provide a means for conveniently measuring 6,15-DK-13,14-DH-PGF$_1\alpha$, a stable metabolite of prostaglandin $I_2$ thought of as reflecting the concentration changes therein, with specificity and high sensitivity.

In view of the circumstances described above, the present inventors conducted investigations with the aim of developing a practical means of assaying 6,15-DK-13,14-DH-PGF$_1\alpha$, and prepared a monoclonal antibody against 6,15-DK-13,14-DH-PGF$_1\alpha$ enabling such assay. The inventors conducted further investigations based on this achievement and developed the present invention.

SUMMARY OF THE INVENTION

The present invention relates to (1) A monoclonal antibody reacting specifically to 6,15-diketo-13,14-dihydro-prostaglandin $F_1\alpha$, (2) A cloned hybridoma which is derived from fusing a spleen cell of a mammal immunized with 6,15-diketo-13,14-dihydro-prostaglandin $F_1\alpha$ with a homogenic or heterogenic lymphoid cell, (3) A method for producing said cloned hybridoma which comprises fusing the homogenic or heterogenic lymphoid cell with the spleen cell from the mammal immunized with 6,15-diketo-13,14-dihydro-prostaglandin $F_1\alpha$ and selecting the desired hybridoma, (4) A method for producing said monoclonal antibody which comprises culturing said cloned hybridoma in either a liquid medium or a mammalian abdominal cavity to produce the monoclonal antibody and collecting the monoclonal antibody, and (5) A method for determining 6,15-diketo-13,14-dihydro-prostaglandin $F_1\alpha$ which comprises using the monoclonal antibody in the above-mentioned item (1).

DETAILED DESCRIPTION OF THE INVENTION

Figure 1:
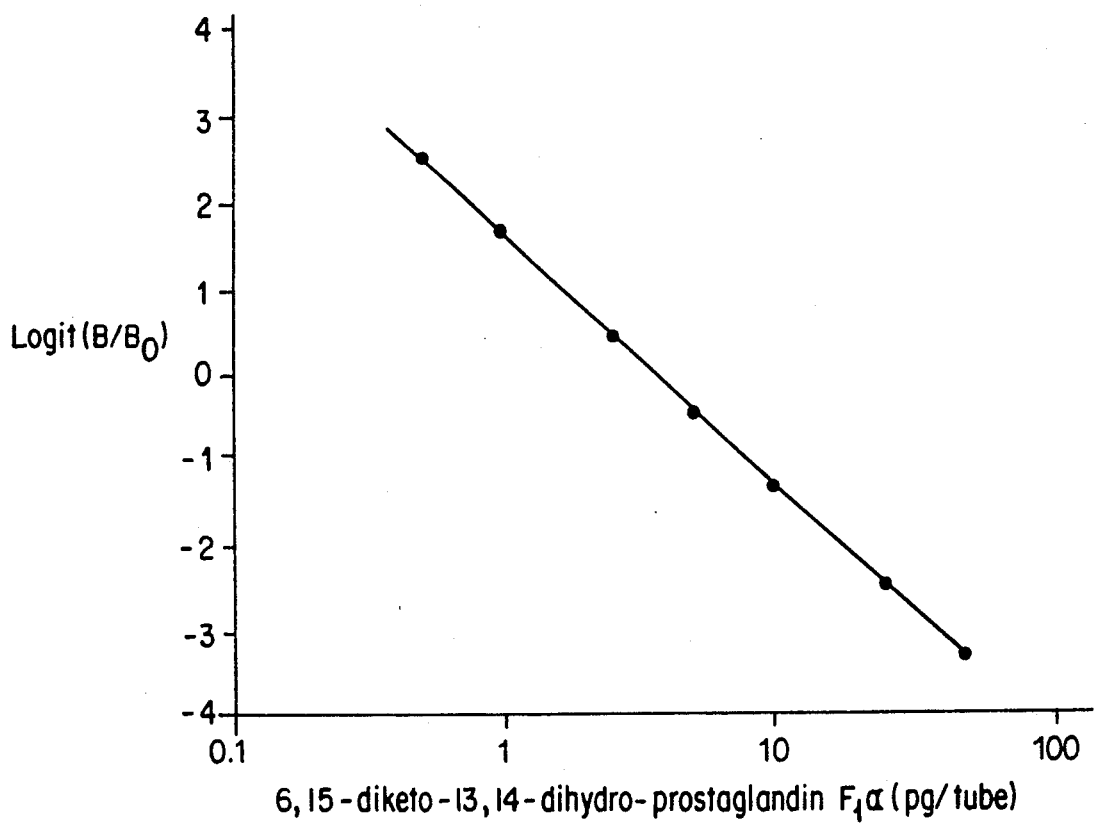
FIG. 1 shows the results of enzyme immunoassay using a monoclonal antibody obtained in Example 3.

The antibody against 6,15-DK-13,14-DH-PGF$_1\alpha$ of the present invention can be prepared by applying a known technique per se.

Commercially available 6,15-DK-13,14-DH-PGF$_1\alpha$ products can be used in the present invention (Cayman Company, distributed by Funakoshi Pharmaceutical Co., Ltd.). The desired antibody can be obtained by inoculating the binding product of 6,15-DK-13,14-DH-PGF$_1\alpha$ and a high molecular carrier substance, as an immunogen, to a non-human warm-blooded animal to form an antibody, and collecting said antibody.

Binding of 6,15-DK-13,14-DH-PGF$_1\alpha$ and the high molecular carrier substance for this purpose can be achieved using a known routine means [e.g., Hormone and Metabolic Research, Vol. 8, p. 241 (1976)], including a method using a dehydrant, such as water-soluble carbodiimide. Examples of the high molecular carrier substance include bovine thyroglobulin, bovine serum albumin, bovine gamma globulin and hemocyanin. The product prepared is dialyzed against water at about 4° C. by a routine means, and may be stored after freezing or freeze drying.

For immunization with the immunogen described above to obtain an antibody, laboratory mammalians such as sheep, goats, rabbits, guinea pigs, rats and mice are used, and among them rats and mice are preferred for obtaining a monoclonal antibody. Concerning the method of immunization, any route is acceptable, including subcutaneous, intraperitoneal, intravenous, intramuscular and intradermal injection, when mice, for instance, are immunized, but it is preferable to inject the immunogen mainly subcutaneously, intraperitoneally or intravenously (particularly subcutaneously). Also, inoculation intervals, inoculum amounts etc. are widely variable and various methods are available, but it is a common practice to inoculate the immunogen 2 to 8 times at 2-week intervals and use splenocytes 1 to 5 days (preferably 2 to 4 days) after final immunization. It is desirable that the inoculum amount be not less than 0.1

μg (preferably 10 to 30 μg) per mouse as the amount of polypeptide for each immunization.

When splenocytes are used as lymphocyte source, provided that the spleen is excised, it is desirable to previously conduct partial blood sampling to confirm increased blood antibody titer, and then make a fusion experiment.

In cell fusion of the above-mentioned lymphocytes and a lymphoblast line, immunized mouse lymphocytes (particularly those derived from splenocytes), for instance, are fused with an appropriate lymphoblast line such as a myeloma cell of the same or different animal species (preferably the same species) having a marker for hypoxanthine-guanine-phosphoribosyl transferase deficiency (HGPRT−) or thymidine kinase deficiency (TK−). A fusogen, such as Sendai virus or polyethylene glycol (PEG), is used for this fusion. It is of course possible to add dimethyl sulfoxide (DMSO) or another fusion promoter. PEG with an average molecular weight of about 1000 to 6000 is used at a concentration of about 10 to 80% and at a treating time of 0.5 to 30 minutes. As a preferable set of conditions, efficient fusion can be achieved by treatment with 35 to 55% PEG6000 for 4 to 10 minutes. The fused cell (hybridoma) can be selectively proliferated using hypoxanthine-aminopterin-thymidine medium [HAT medium; Nature, Vol. 256, p. 495 (1975)] or another medium.

Mouse sera and the culture supernatant of proliferated cells can be screened for production of the desired antibody; antibody titer screening can be carried out as follows. Specifically, antibody titer can be determined by radioimmunoassay (RIA method), enzyme immunoassay (EIA method) and other methods, which are widely modifiable. As a preferred mode of assay, the method based on EIA is described below. To anti-mouse immunoglobulin, previously immobilized to a solid phase by a conventional method (the use of a 96-well microtiter plate as a solid phase is advantageous because it allows rapid assay using a plate reader etc.), the subject culture supernatant or mouse serum is added, followed by reaction at constant temperature ("constant temperature," as used hereinafter, means 4° to 40° C.) for a given period. The reaction product is then thoroughly washed, after which enzyme-labeled 6,15-DK-13,14-DH-PGF$_1\alpha$ is added, followed by reaction at constant temperature for a given period. After the reaction product is thoroughly washed, an enzyme substrate is added, followed by reaction at constant temperature for a given period, after which the coloring product can be measured by absorbance or fluorescence intensity.

With respect to cells in the wells in which proliferation occurred on the selection medium, antibody activity against 6,15-DK-13,14-DH-PGF$_1\alpha$ was present and specific activity was noted, it is desirable to conduct cloning by limiting dilution analysis and other means. The supernatant of the cloned cells is screened in the same manner as above to increase the number of cells with high antibody titer, whereby hybridoma clones producing a monoclonal antibody are obtained.

The hybridoma thus cloned is proliferated in liquid medium or a mammalian abdominal cavity. For example, said monoclonal antibody can be obtained from culture broth after cultivation for 2 to 10 days, preferably 3 to 5 days, in a liquid medium, such as that prepared by adding 0.1 to 40% bovine serum to RPMI-1640 medium. An antibody with a titer much higher than that obtained with cell culture supernatant can be obtained in large amounts with high efficiency by inoculating the cloned hybridoma to the abdominal cavity of an appropriate mammal, such as a mouse, to allow cell proliferation, and then collecting ascitic fluid. For this purpose, in the case of a mouse, for instance, $1 \times 10^4$ to $1 \times 10^7$, preferably $5 \times 10^5$ to $2 \times 10^6$ hybrid cells are intraperitoneally or otherwise inoculated to BALB/c or another line of mice previously inoculated with mineral oil etc., ascitic fluid being collected 7 to 20 days (preferably 10 to 14 days) later. From the ascitic fluid, in which the antibody was produced and accumulated, the desired monoclonal antibody can easily be isolated as pure immunoglobulin by ammonium sulfate fractionation, DEAE-cellulose column chromatography or another method.

The monoclonal antibody in the present invention may be immunoglobulin or a fraction thereof [e.g., F(ab')$_2$, Fab' or Fab].

In the immunochemical assay for 6,15-DK-13,14-DH-PGF$_1\alpha$ in the present invention, the competitive method is usually used. The competitive method is defined as a method in which a given amount of a subject solution containing an unknown amount of 6,15-DK-13,14-DH-PGF$_1\alpha$ and a given amount of marker-labeled 6,15-DK-13,14-DH-PGF$_1\alpha$ are subjected to competitive reaction with a given amount of the corresponding antibody, and the activity of the antibody-bound marker or unbound marker is determined, to determine the amount of 6,15-DK-13,14-DH-PGF$_1\alpha$ in the subject solution.

As an example application of the enzyme immunoassay method according to the present invention, the use of horseradish peroxidase (hereinafter also referred to as HRP for short) as a marker is specifically described below, which is not to be construed as limitative.

①: To the subject solution, add a given amount of HRP-labeled 6,15-DK-13,14-DH-PGF$_1\alpha$ and mix.

②: Add an antibody in an amount corresponding to the given amount of the labeled 6,15-DK-13,14-DH-PGF$_1\alpha$, mix and carry out a competitive reaction.

③: To the reaction product obtained in ②, add a solid phase on which is fixed a foreign antibody against the immunoglobulin of the animal used to prepare the antibody of ② (hereinafter referred to as anti-seed antibody for short), and carry out reaction at constant temperature for a given period.

④: Wash the solid phase thoroughly and determine the HRP activity.

⑤: Perform procedures ① through ④ above on a given amount of standard solution and draw a standard curve.

⑥: Apply the HRP activity obtained with the unknown amount of assay subject (subject solution) to the standard curve to determine the amount of 6,15-DK-13,14-DH-PGF$_1\alpha$ in the assay subject.

Examples of subject solutions include biological samples such as those of blood plasma, serum, urine, spinal fluid and tissue extracts.

Examples of markers include enzymes, radioisotopes, fluorescent substances and luminescent substances.

Examples of preferable radioisotopes include $^{125}$I, $^{131}$I, $^3$H and $^{14}$C. The enzyme is preferably stable and of high specific activity; examples of such enzymes include 1) carbohydrases [e.g., glycosidases (e.g., β-galactosidase, β-glycosidase, β-glucurosidase, β-fructosidase, α-galactosidase, α-glucosidase, α-mannosidase), amylases (e.g., α-amylase, β-amylase, isoamylase, glucoamylase, Taka amylase A) cellulase, lysozyme], 2) amylases (e.g., urease, asparaginase), 3) esterases [e.g., choline esterases (e.g., acetylcholine esterase), phosphatases (e.g., alkaline phosphatase), sulfatase, lipase], 4) nucleases (e.g., deoxyribonuclease, ribonuclease), 5) iron-porphyrin enzymes (e.g., catalase, peroxidase, cytochrome oxidase), 6) copper enzymes (e.g., tyrosinase, ascorbic acid oxidase), and 7) dehydrogenases (e.g., alcohol dehydrogenase, malic acid dehydrogenase, lactic acid dehydrogenase, isocitric acid dehydrogenase). Examples of fluorescent substances include fluorescamine and fluorescence isothiocyanate. Examples of luminescent substances include luminol, luminol derivatives, luciferin and lucigenin. Of these markers, enzymes, particularly peroxidase can be used especially advantageously.

Binding of 6,15-DK-13,14-DH-PGF$_1\alpha$ and marker can be achieved by a conventional method, such as the use of a condensing agent, e.g., water-soluble carbodiimide.

The monoclonal antibody of the present invention makes it possible to conveniently measure 6,15-diketo-13,14-dihydro-prostaglandin F$_1\alpha$, a stable metabolite of prostaglandin I$_2$ thought of as reflecting the concentration changes therein, with specificity and high sensitivity. It is useful in determining the content of prostaglandin I$_2$, which exhibits platelet aggregating inhibitory activity, vasodilating activity and other activities, in biological samples.

The monoclonal antibody of the present invention hardly reacts with other arachidonic acid metabolite, for example, 6-keto-PGF$_1\alpha$, 2,3-dinor-6-keto-PGF$_1\alpha$, 6-keto-PGE$_1$, PGB$_2$, PGD$_2$, PGE$_1$, PGE$_2$, PGF$_1\alpha$, PGF$_2\alpha$, TXB$_2$, 11-dehydro-TXB$_2$, 15-keto-PGF$_2\alpha$, 13,14-dihydro-15-keto-PGE$_1$ or 13,14-dihydro-15-keto-PGF$_2\alpha$.

To carry out a specific immunochemical assay based on the competitive method, a sample containing an unknown amount of 6,15-DK-13,14-DH-PGF$_1\alpha$, for instance, is reacted with a given amount of labeled 6,15-DK-13,14-DH-PGF$_1\alpha$ and a given amount of monoclonal antibody, after which a solid phase, previously bound with anti-seed antibody physically or chemically, is added to react. Then, usually, after washing thoroughly the solid the marker activity bound to the solid phase is measured. When the marker is a radioisotope, its activity is measured using a well counter or a liquid scintillation counter. When the marker is an enzyme, a substrate is added, and after a while enzyme activity is determined by a colorimetric or fluorometric method. Whether the marker is a fluorescent or luminescent substance, each is measured by a known method.

When a biological sample, particularly a serum or plasma sample, is assayed for a trace amount of 6,15-DK-14,14-DH-PGF$_1\alpha$ with high precision, sample pretreatment is often necessary. Examples of sample concentrating procedures include the extraction concentration method using an organic solvent, the method using a cartridge type column of octadecylsilane (ODS) and the method using an antibody-bound affinity column. Of these methods, that using a packed cartridge with ODS or another organic silicon immobilized thereon is commonly widely used.

Specifically, when the sample is a body fluid such as plasma, serum or urine, it is applied to the cartridge after being adjusted to acidic pH. In the case of an organ or tissue section, it is extracted with an appropriate organic solvent, such as alcohol or chloroform, after which it is adjusted to acidic pH and then applied to the cartridge. After such a sample solution is passed through the cartridge for adsorption, it is washed and then eluted with an appropriate eluent, such as alcohol, ethyl acetate, acetonitrile or a hydrate thereof, to elute the adsorbed target substance. The eluate thus obtained is then evaporated to dryness either in N$_2$ gas or under reduced pressure. The residue is then dissolved in a buffer; the resulting solution, as a subject solution, is usually subjected to RIA, EIA or another immunochemical assay.

Hybridoma Dk 501, obtained in Example 1 below, has been deposited under accession number FERM BP-3464 at the Fermentation Research Institute of the Agency of Industrial Technology, Ministry of International Trade and Industry, since Jun. 25, 1991, under the Budapest treaty and has also been deposited under accession number IFO 50342 at the Institute for Fermentation, Osaka (IFO), since Jun. 28, 1991.

EXAMPLES

The present invention is hereinafter described in more detail by means of the following examples, but the invention is not limited to them.

EXAMPLE 1 (Establishment of Hybridoma)

A solution of 500 µg of 6,15-DK-13,14-DH-PGF$_1\alpha$ in 80% dioxane (300 µl), 750 µg of 1-ethyl-3-(3-dimethylaminopropyl)carbodiimide hydrochloride and 500 µg of N-hydroxysuccinimide were reacted at room temperature for 3 hours, after which 1 ml of purified water was added, followed by three cycles of extraction with 2 ml of ethyl acetate. The extract was then evaporated to dryness in nitrogen gas. To the dry product, 3 mg of bovine serum albumin (BSA) in solution in 1 ml of physiological saline was added, followed by 20 hours of reaction at 4° C.; the reaction product was then dialyzed against physiological saline. This reaction product was used as an immunogen. In each of five BALB/c mice, a solution of 100 µg of a conjugate of 6,15-DK-13,14-DH-PGF$_1\alpha$ and BSA in 0.5 ml of physiological saline, containing 0.5 ml of Freund's complete adjuvant suspended therein, was intraperitoneally injected. Two to 12 weeks later, 50 µg of a conjugate of 6,15-DK-13,14-DH-PGF$_1\alpha$ and BSA in solution in 0.1 ml of physiological saline was injected for booster immunization in each mouse via the tail vein. At 3 days following final immunization, mouse splenocytes were taken out for cell fusion.

The collected splenocytes (1.0×10$^8$) and myeloma cells FO (1.0×10$^7$) were mixed in RPMI-1640 medium and centrifuged at 1,000 rpm for 5 minutes. To the resulting sediment, 1 ml of 50% polyethylene glycol 1500 was gradually added at 37° C. over a 1-minute period, and the cells were allowed to fuse. After 7 ml of RPMI-1640 medium at 37° C. was added over a 5-minute period, the mixture was centrifuged. The resulting fused cells were diluted with HAT medium and dispensed to 96-well microplates at 0.1 ml per well, after which they were cultivated with half the HAT medium replaced with fresh HAT medium at intervals of 2 to 3 days. After 7 to 14 days, hybridoma proliferation occurred in all 288 wells, 25% of which (72/288) proved to contain anti-6,15-DK-13,14-DH-PGF$_1\alpha$ antibody produced therein.

The cells from the wells with the highest antibody titer were cloned by limiting dilution analysis. Specifically, 10$^5$/well BALB/c mouse thymocytes, as feeder cells, and 1/well hybridoma were added to the wells and cultivated in HT medium. This procedure was repeated in two cycles. The clone which produced the desired antibody most stably and most richly was selected via cloning and named Dk 501 (IFO 50342, FERM BP-3464).

The antibody titer of the clone was determined as follows. To a microplate with an anti-mouse immunoglobulinG (IgG) antibody immobilized thereon, 100 μl of the hybridoma culture supernatant was added, followed by reaction at room temperature for 1 hour. After plate washing, peroxidase-labeled 6,15-DK-13,14-DH-PGF$_1\alpha$ was added, followed by reaction at room temperature for 1 hour. After plate washing again, a solution of the enzyme substrate o-phenylenediamine was added, and its absorbance determined, to obtain the antibody titer of the hybridoma culture supernatant.

Peroxidase-labeled 6,15-DK-13,14-DH-PGF$_1\alpha$ was prepared as follows. A solution of 200 μg of 6,15-DK-13,14-DH-PGF$_1\alpha$ in 80% dioxane (300 μl), 300 μg of 1-ethyl-3-(3-dimethylaminopropyl)carbodiimide hydrochloride and 200 μg of N-hydroxysuccinimide were reacted at room temperature for 3 hours, after which 1 ml of purified water was added, followed by three cycles of extraction with 2 ml of ethyl acetate. The extract was then evaporated to dryness in nitrogen gas. To the dry product, 1 mg of peroxidase in solution in 0.2 ml of physiological saline was added, followed by 20 hours of reaction at 4° C.; the reaction product was purified by gel filtration with Superose 12.

EXAMPLE 2 (Production of Monoclonal Antibody)

To BALB/c mice, previously treated by intraperitoneal administration of 0.5 ml of pristane, $5 \times 10^6$ Dk 501 hybrid cells in suspension in 0.5 ml of RPMI-1640 were intraperitoneally injected. 10 to 14 days later, the retained ascitic fluid was collected and purified using Protein-A Cellulofine, to yield the monoclonal antibody Dk 501. The yield of the monoclonal antibody Dk 501 was 15 mg per ml of ascitic fluid.

EXAMPLE 3 (Specificity of Monoclonal Antibody)

The isotype of the monoclonal antibody (Dk 501) established in Example 1 was determined to be IgG$_1$ by the Ouchterlony method. Its binding specificity was determined by examining its cross reactivity against other arachidonic acid metabolites by enzyme immunoassay. The results are shown in Table 1. This monoclonal antibody hardly reacted with other arachidonic acid metabolites. This monoclonal antibody is therefore identified as a monoclonal antibody which specifically reacts to 6,15-DK-13,14-DH-PGF$_1\alpha$.

TABLE 1

| Arachidonic acid metabolite | Cross reactivity (%) |
|---|---|
| 6,15-diketo-13,14-dihydro-PGF$_1\alpha$ | 100 |
| 6-keto-PGF$_1\alpha$ | 0.28 |
| 2,3-dinor-6-keto-PGF$_1\alpha$ | 0.03 |
| 6-keto-PGE$_1$ | 0.03 |
| PGB$_2$ | 0.02 |
| PGD$_2$ | 0.001 |
| PGE$_1$ | 0.009 |
| PGE$_2$ | 0.004 |
| PGF$_1\alpha$ | 0.009 |
| PGF$_2\alpha$ | 0.002 |
| TXB$_2$ | 0.001 |
| 11-dehydro-TXB$_2$ | 0.002 |
| 15-keto-PGF$_2\alpha$ | 0.63 |
| 13,14-dihydro-15-keto-PGE$_1$ | 0.37 |
| 13,14-dihydro-15-keto-PGF$_2\alpha$ | 0.30 |

The enzyme immunoassay described above was conducted as follows. 100 μl of either a standard 6,15-DK-13,14-DH-PGF$_1\alpha$ solution or a standard solution of another arachidonic acid metabolite, 100 μl of a solution of peroxidase-labeled 6,15-DK-13,14-DH-PGF$_1\alpha$ and 100 μl of a solution of the mouse monoclonal anti-6,15-diketo-13,14-dihydro-prostaglandin F$_1\alpha$ antibody (Dk 501) obtained in Examples 1 and 2 were mixed, and a solid phase bound with anti-mouse IgG antibody was added, followed by reaction at 4° C. for 20 hours. After plate washing, 500 μl of a 0.1M citrate buffer containing 0.02% hydrogen peroxide and 0.26% o-phenylenediamine was added, followed by reaction at room temperature for 1 hour. After 1 ml of 1N sulfuric acid was added to terminate the reaction, absorbance at 492 nm was determined.

The detection limit of this enzyme immunoassay using the monoclonal antibody was 0.5 pg/tube (1.3 fmol), indicating very high sensitivity (FIG. 1). In FIG. 1, Bo in B/Bo is the enzyme activity bound to the solid phase in the absence of 6,15-DK-13,14-DH-PGF$_1\alpha$; B is the enzyme activity bound to the solid phase in the presence of 6,15-DK-13,14-DH-PGF$_1\alpha$.

EXAMPLE 4 (Assay of Blood Plasma for 6,15-diketo-13,14-dihydro-PGF$_{1\alpha}$)

(1) Preparation of Immobilized Antibody Column

After inclusion in a dialytic membrane, 50 mg of anti-6,15-diketo-13,14-dihydro-PGF$_{1\alpha}$ monoclonal antibody (Dk 501) was dialyzed against 0.1M carbonate buffer (pH 8.5) at 4° C. for 24 hours. The antibody was immobilized by a known method as follows. 5 g of Sepharose 4B, previously activated with cyanogen bromide, was washed with 1000 ml of 1 mM hydrochloric acid and then with 100 ml of 0.1M carbonate buffer (pH 8.5). To this washed cyanogen-bromide-activated Sepharose 4B, the dialyzed monoclonal antibody was added, followed by stirring at room temperature for 3 hours. After blocking the unreacted active groups using 0.1M Tris buffer (pH 8.5), the mixture was washed with purified water and methanol. The resulting monoclonal-antibody-bound Sepharose 4B was diluted with Sepharose 4B to an antibody content of 300 μg per ml of gel. The diluted antibody-bound Sepharose 4B, in an amount of 0.7 ml as of gel volume, was packed in a polypropylene column (Sepacol Mini PP, produced by Seikagaku Kogyo). The column was washed with 0.1M phosphate-buffered saline (pH 7.5) and then stored at 4° C.

(2) Plasma Sample Pre-Treatment Using the Immobilized Antibody Column

After washing the immobilized antibody column with 5 ml of a 0.1M phosphate-buffered saline (pH 7.5) containing 0.05% Triton X-100, a plasma sample, whether or not supplemented with various concentrations of a standard preparation of 6,15-diketo-13,14-dihydro-PGF$_{1\alpha}$, was applied to the column. After the column was washed with 5 ml of a 0.1M phosphate-buffered saline (pH 7.5) containing 0.05% Triton X-100, 15 ml of purified water and 35 ml of a mixture of methanol and purified water (3:7), elution was conducted with 5 ml of 95% methanol. The resulting eluate was evaporated to dryness under nitrogen gas, after which it was dissolved in 0.5 ml of 0.1M phosphate-buffered saline to yield an enzyme immunoassay sample.

Figure 2A:
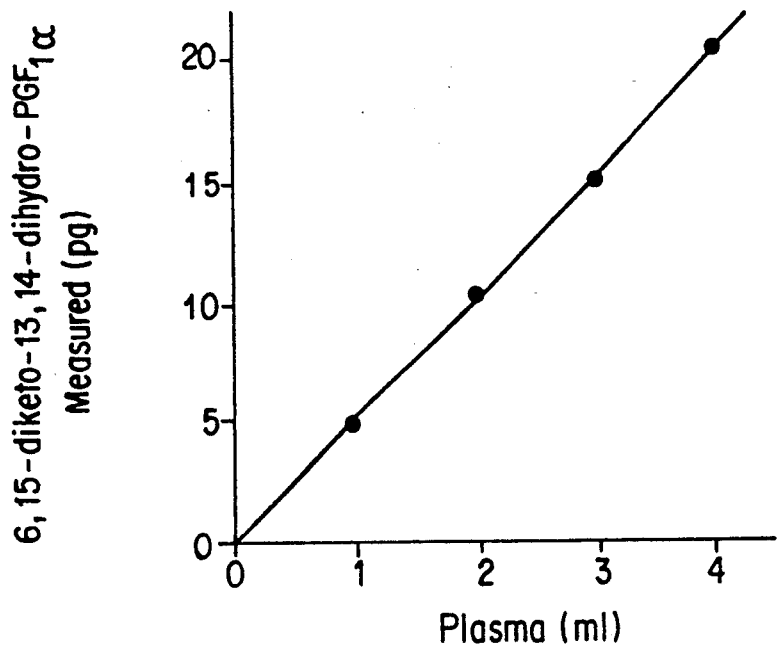
FIG. 2 shows the results of the assay method based on plasma sample pre-treatment using an immobilized antibody column obtained in Example 4.
Figure 2B:
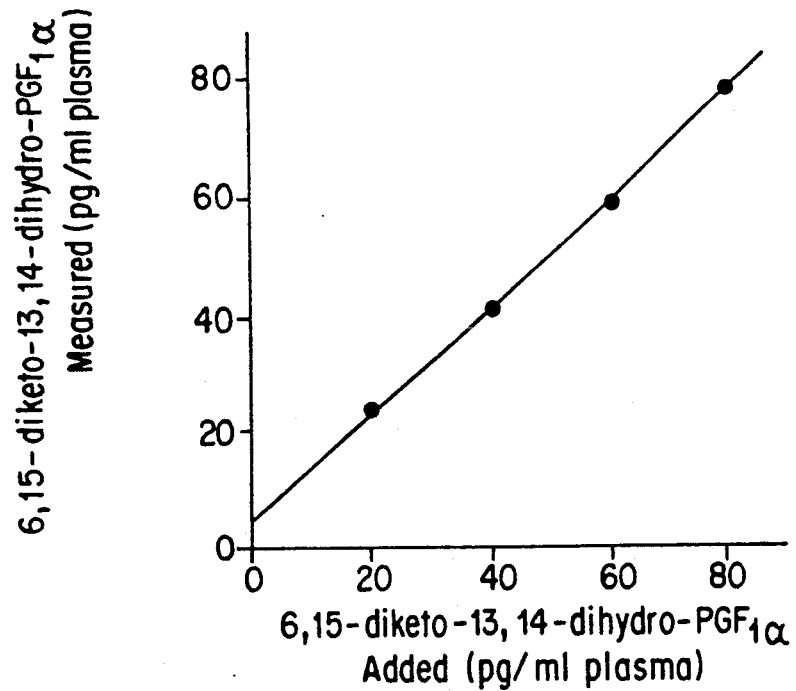

FIG. 2 shows the validity of the present assay method based on plasma sample pre-treatment using the immobilized antibody column. As seen in FIG. 2, the experimentally found value increased 1, 2, 3 and 4 fold as the amount of plasma sample applied to the column was increased 1, 2, 3 and 4 fold, indicating a good linearity in simple regression analysis (FIG. 2(A)). A good linearity was also obtained in the experiment with plasma samples supplemented with the standard preparation, a recovery rate of over 90% on average obtained (FIG. 2(B)).

The following references, which are refered to for their disclosures at various points in this application, are incorporated herein by reference.

1. ALAN R. BRASH et al., The Journal of Pharmacology and Experimental Therapeutics, Vol. 226, p.78 (1983)
2. FitzGeld, G. A. et al., Circulation, 67, 1174–1177 (1983)
3. Carlo Patrono et al., Advances in Prostaglandin, Thromboxane, and Leukotriene Research, Vol. 15, p.71–73 (1985), edited by O. Hayaishi and S. Yamamoto, Raven Press, New York
4. M. Suzuki et al., Japanese Journal of Clinical Medicine, Vol. 43, p.1082 (1985)
5. C. Patrono et al., Clinical Research, Vol. 29, p.276A (1981)

We claim:

1. A monoclonal antibody reacting specifically to 6,15-diketo-13,14-dihydro-prostaglandin $F_1\alpha$, wherein said antibody does not significantly react with 6-keto-$PGF_1\alpha$, 2,3-dinor-6-keto-$PGF_1\alpha$, 6-keto-$PGE_1$, $PGB_2$, $PGD_2$, $PGE_1$, $PGE_2$, $PGF_1\alpha$, $PGF_2\alpha$, $TXB_2$, 11-dehydro-$TXB_2$, 15-keto-$PGF_2\alpha$, 13,14-dihydro-15-keto-$PGE_1$ or 13,14-dihydro-15-keto-$PGF_2\alpha$.

2. A cloned hybridoma capable of producing the antibody according to claim 1 which is derived from fusing a spleen cell of a mammal immunized with 6,15-diketo-13,14-dihydro-prostaglandin $F_1\alpha$ with a homogenic or heterogenic lymphoid cell.

3. The cloned hybridoma according to claim 2, wherein the 6,15-diketo-13,14-dihydro-prostaglandin $F_1\alpha$ is conjugated to a high molecular carrier substance.

4. The cloned hybridoma according to claim 3, wherein the high molecular carrier substance is a protein.

5. The cloned hybridoma according to claim 4, wherein the protein is bovine serum albumin.

6. The cloned hybridoma according to claim 2, wherein the mammal is a mouse.

7. The cloned hybridoma according to claim 2, wherein the lymphoid cell is a myeloma cell.

8. The cloned hybridoma according to claim 2, which is Dk 501 (FERM BP-3464).

9. A method for producing said cloned hybridoma according to claim 2, which comprises (1) fusing the homogenic or heterogenic lymphoid cell with the spleen cell from the mammal immunized with 6,15-diketo-13,14-dihydro-prostaglandin $F_1\alpha$ and
(2) selecting the desired hybridoma 10. A method for producing said monoclonal antibody according to claim 1, which comprises (1) culturing a cloned hybridoma, derived from fusing a spleen cell of a mammal immunized with 6,15-diketo-13,14-dihydro-prostaglandin $F_1\alpha$ with a homogenic or heterogenic lymphoid cell in either a liquid medium or a mammalian abdominal cavity to produce the monoclonal antibody and
(2) collecting the monoclonal antibody.

11. The method according to claim 10, wherein the mammal is immunized with the 6,15-diketo-13,14-dihydro-prostaglandin $F_1\alpha$ conjugated to a high molecular carrier substance.

12. A method for determining 6,15-diketo-13,14-dihydro-prostaglandin $F_1\alpha$ which comprises using the monoclonal antibody according to claim 1.

13. The method according to claim 12, wherein the monoclonal antibody is produced by a cloned hybridoma which is derived from fusing a spleen cell of a mammal immunized with 6,15-diketo-13,14-dihydro-prostaglandin $F_1\alpha$ conjugated to a high molecular carrier substance with a homogenic or heterogenic lymphoid cell.

14. The method according to claim 12, which is carried out by an enzyme immunoassay.

15. The method according to claim 12, wherein the monoclonal antibody is labeled with enzyme.

16. The method according to claim 11, wherein the high molecular carrier substance is a protein.

17. The method according to claim 16, wherein the protein is bovine serum albumin.

18. The method according to claim 10, wherein the lymphoid cell is a myeloma cell.

19. The method according to claim 10, wherein the cloned hybridoma is Dk 501 (FERM BP-3464).

20. The method according to claim 10, wherein the mammal is a mouse.

21. The method according to claim 13, wherein the high molecular carrier substance is a protein.

22. The method according to claim 21, wherein the protein is bovine serum albumin.

23. The method according to claim 13, wherein the lymphoid cell is a myeloma cell.

24. The method according to claim 13, wherein the cloned hybridoma is Dk 501 (FERM BP-3464).

25. The method according to claim 13, wherein the mammal is a mouse.

* * * * *